United States Patent [19]
Weathers et al.

[11] Patent Number: 5,413,928
[45] Date of Patent: May 9, 1995

[54] PROCESS FOR EXTRACTING ENHANCED AMOUNTS OF PLANT SECONDARY METABOLITES WITH LIMITED LOSS OF PLANT VIABILITY

[75] Inventors: Pamela J. Weathers, Stow; Ronald D. Cheetham, Holden; Alexander DiIorio, Worcester, all of Mass.

[73] Assignee: Worcester Polytechnic Institute, Worcester, Mass.

[21] Appl. No.: 719,183

[22] Filed: Jun. 21, 1991

[51] Int. Cl.$^6$ .................. C12N 5/00; C12N 5/02; C12P 17/02
[52] U.S. Cl. .................. 435/240.4; 435/240.45; 435/240.46; 435/123; 549/510; 424/195.1
[58] Field of Search .................. 424/195.1; 435/123, 435/240.4, 240.45, 240.46; 549/510

[56] References Cited

U.S. PATENT DOCUMENTS

| | | | |
|---|---|---|---|
| 4,952,603 | 8/1990 | ElFeraly et al. | 514/450 |
| 5,019,504 | 5/1991 | Christen et al. | 435/123 |

FOREIGN PATENT DOCUMENTS

| | | |
|---|---|---|
| 0062457 | 3/1982 | European Pat. Off. . |
| 0071999 | 8/1982 | European Pat. Off. . |
| 0200225 | 4/1986 | European Pat. Off. . |
| 0378921 | 12/1989 | European Pat. Off. . |
| 2200134 | 12/1987 | United Kingdom . |

OTHER PUBLICATIONS

Derwent Abstract, accession No. 90-14605, P. J. Weathers et al, 1989.
Weathers, P. J., et al., "A Bioreactor for Differentiated Plant Tissues," *Proceedings of the Biotech USA Conference*, pp. 247-256 (Oct. 1989).
Signs, M. W. and Flores, H. E., "The Biosynthetic Potential of Plant Roots," *BioEssays*, 12(1):7-13 (1990).
Nair, M. S. R., et al., "Production of Artemisinin in Tissue Cultures of Artemisia Annua," *J. of Natural Prod.*, 49(3):504-507 (1986).
Flores, H. E., et al., "Production of Polyacetylenes and Thiophenes in Heterotrophic and Photosynthetic Root Cultures of Asteraceae," *Bioactive Molecules*, 7:233-254 (1988).
Hamill, J. D., et al., "New Routes to Plant Secondary Products," *BioTechnology*, 5:800-804 (1987).
Parr, A. J., "The Production of Secondary Metabolites by Plant Cell Cultures," *J. of Biotechnology*, 10:1-26 (1989).
International Search Report, PCT/US92/05211, (13.10.92).
Dietrich Knorr, et al., *Food Technology*, 135-142, Oct. 1985.
Nigel John Kilby and Christopher Stuart Hunter, *Appl. Microbiol. Biotechnol*, 34:478-480 (1991).
Peter Brodelius, *Appl. Microbiol. Biotechnol*, 27:561-566 (1988).
Yocheved Toprover and Z. Glinka, *Physiol. Plant*, 37:131-134 (1976).
Hansruedi Felix, *Analytical Biochemistry*, 120:211-234 (1982).
Alexander A. DiIorio, et al., Extended Abstract for American Institute of Chemical Engineers Meeting Nov. 1990, "Secondary Product Release in Transformed Root Cultures of Beta yulgaris".
P. J. Weathers, et al., Abstract for Jun. 1990 meeting in Amsterdam, "Recovery of Secondary Metabolites with Minimal Loss of Tissue Viability".
P. J. Weathers, et al., *Progress in Plant Cellular and Molecular Biology*, (1990) eds. H. J. J. Nijkamp, L. H. W. van der Plas, and J. van Aartrijk, Kluwer Academic Publ., Netherlands.
Pamela J. Weather, et al., *Proceedings of Biotech USA Conference*, Oct. 1989, San Francisco, Calif. "A Bioreactor for Differentiated Plant Tissues".
J. Renaudin, Plant Science Lett. 22(198):59-69.
M. Shuler, et al., JAOCS, 61(1984): 1724-1728.
Chem. Abstracts. 104(19):165674b; P. Lundberg, et al., 1986.

*Primary Examiner*—John W. Rollins
*Attorney, Agent, or Firm*—Hamilton, Brook, Smith & Reynolds

[57] ABSTRACT

A process for extracting enhanced amounts of a plant secondary metabolite from plant tissue with limited loss of tissue viability by reversibly permeabilizing the tissue membrane is disclosed.

12 Claims, No Drawings

PROCESS FOR EXTRACTING ENHANCED AMOUNTS OF PLANT SECONDARY METABOLITES WITH LIMITED LOSS OF PLANT VIABILITY

GOVERNMENT SUPPORT

Work described herein was supported in part by funding from the National Science Foundation. The United States Government has rights in the subject invention.

BACKGROUND OF THE INVENTION

Plants grown in vitro can provide a major source of specialty chemicals, which are plant secondary metabolites. For example, artemisinin, a terpenoid found in the herb, Artemisia annua, is a promising therapeutic for treatment of malaria. However, this highly effective compound is produced by native plants in minute quantities, and by tissue cultured plants at levels significantly less than the best native plants. Efforts to obtain higher production levels in either native plants or their cultured tissues would make therapeutic use of artemisinin on a large scale, a reality.

Taxol is a novel diterpene isolated primarily from the bark of Taxus brevifolia and other species of Taxus. Although knowledge about the sites of taxol biosynthesis and distribution is limited, it is known that the product is next most abundant in the root. Taxol has been shown to be an especially effective antitumor agent. However, there is considerable difficulty in obtaining sufficient quantities of taxol for clinical testing. The yield of taxol from Taxus bark is low (500 gm per 10,000 lbs bark), and native plants are rapidly dwindling in number. Like many woody plants the genus is recalcitrant to propagation by in vitro culture, rooted cuttings, or reseeding for reforestation. Further therapeutic development will depend largely on solving problems of biomass supply. Because Taxus biomass grows so slowly and taxol is produced at low levels in the tissues, the biomass is valuable.

Except for shikonin and berberine, there has been little success in the profitable production of secondary metabolites from plant cultures. The lack of success is due in part to the fact that these chemicals are present only in small amounts within the plant. In addition, in vitro and in vivo cloning of plants, especially woody plants is extremely difficult, because of slow growth rates, reduced or lack of rooting ability, frequent systemic microbial contamination, phenotypic instability, and phenolics build-up. Micropropagation is no different.

There has been some success in the establishment of undifferentiated callus and cell culture lines for the production of secondary metabolites. (See, for example, U.S. Pat. No. 5,019,504 entitled, "Production of taxol or taxol-like compounds in cell culture," by Christen et al.) However, secondary metabolism is frequently linked to differentiation. Therefore, most undifferentiated cultures are not useful for producing secondary metabolites.

Most secondary metabolites of plants accumulate within the plant tissue and are not readily exported into the growth medium. In addition, most secondary metabolites are chemically complex and therefore are difficult to synthesize. Thus, there is a need to develop nondestructive methods whereby products produced by plant tissues can be easily recovered for processing while still retaining the valuable biomass for additional product biosynthesis.

SUMMARY OF THE INVENTION

The subject invention relates to a process for extracting enhanced amounts of a plant secondary metabolite from plant tissue with limited loss of tissue viability by reversibly permeabilizing the plant tissue membrane. The process includes three steps: 1) destabilizing plant tissue membrane to effect partial release of a plant secondary metabolite; 2) removing the secondary metabolite to enhance the diffusion gradient and thereby increase secondary metabolite efflux; and 3) restabilizing the plant tissue membrane to inhibit secondary metabolite release.

In order to obtain enhanced amounts of a plant secondary metabolite, it is preferred that the tissue is differentiated. Plant roots including genetically transformed hairy roots provide an especially preferred tissue for obtaining many plant secondary metabolites. In addition, the plant tissue should be actively synthesizing the metabolite or contain high levels of stored metabolite. Generally, plant cultures which are growing in late exponential growth phase and stationary phase produce enhanced amounts of secondary metabolite. A particularly useful method of obtaining plant tissue which contains enhanced amounts of secondary metabolite is by culturing in a nutrient mist bioreactor.

According to the method of the subject invention, plant tissue membrane is destabilized to effect partial release of the plant secondary metabolite from the tissue. Partial release is important, because if the level of secondary metabolite released is too high, the tissue loses viability. Destabilization of plant tissue membranes can be accomplished by any of a number of techniques, performed alone or in combination. For example, the plant tissue membrane can be exposed to elevated temperatures for various periods of time. Culturing plant tissue in temperatures in the range of 25°–45° C. for times ranging generally from 1 minute to 2 hours is useful for obtaining partial release of most secondary metabolites, while maintaining plant tissue viability.

Alternatively, a plant membrane can be contacted with a permeabilizing agent at an appropriate temperature and for an appropriate length of time. An example of a permeabilizing agent is a substance which prevents the binding of divalent cations to plant cell membranes. Particularly useful permeabilizing agents are $(NH_4)_2SO_4$ and EDTA. Permeabilizing agents can be used alone or in combination with other permeabilizing agents and/or other methods of destabilizing the plant cell membrane. Membrane destabilization can also be accomplished by excluding membrane stabilizers (e.g., divalent cations) from the culture medium.

Subsequent to destabilizing the plant membrane, solvents can optionally be added to plant culture medium to effect greater extraction of secondary metabolites. For example, some secondary metabolites are nonpolar compounds and therefore are not soluble in aqueous solutions, such as the culture medium. Therefore, a nonaqueous solvent, which does not decrease the plant tissue viability, can be added to the plant tissue surroundings (e.g., the culture medium) to enhance extraction of nonpolar secondary metabolites. Alternatively, the permeabilizing agent itself can be a nonaqueous solvent.

In the next step of the subject method, secondary metabolite is removed from the plant tissue surroundings. For example, removal of the released secondary product can be accomplished by exchanging the medium containing the released product with fresh medium. As near continuous removal of released product is approached, secondary metabolite release is increased.

In the final step of the method of the invention, the plant tissue membrane is restabilized to inhibit secondary metabolite release and to enhance plant tissue viability. Restabilization of plant tissue membranes can be accomplished by any of a number of techniques, performed alone or in combination. One approach is to remove the condition which promoted destabilization. For example, the temperature of the culture medium can be cooled (e.g., to room temperature). Alternatively, the destabilizing agent can be removed. Further, divalent cations can be introduced into cultures which were destabilized by being cultured in medium which lacked divalent cations, or other plant cell membrane components which contained a permeabilizing agent. Addition of sterols or other components of cell membranes can also effectively restabilize plant cell membranes and enhance plant tissue viability.

The disclosed methods for secondary metabolite release can be applied to a viable culture without significant loss of biomass. This biomass is therefore conserved and available for further permeabilizations to obtain product release without the need to accumulate more biomass, which could require weeks to accomplish in a large scale bioreactor. Therefore, the cost of processing large amounts of biomass in batch production is effectively reduced. In addition, the degree of selectivity toward specific products offered by the choice of destabilization methods provides additional control over process development.

DETAILED DESCRIPTION OF THE INVENTION

The subject invention relates to processes for extracting enhanced amounts of a plant secondary metabolite (also referred to as secondary product) from plant tissue with limited loss of tissue viability. Plant secondary metabolites are chemical compounds synthesized in plants, that are not specifically required by the plant to maintain cellular processes. Examples of secondary metabolites include flavors (e.g., spearmint, peppermint), fragrances (e.g., jasmine), medicinals (e.g., taxol, artemisinin, ginkgolides, vinblastine, vincristine) and cidal agents (e.g. thiophenes, thiarubrines). Most secondary metabolites accumulate in plant vacuoles and are not readily released from the plant.

Some secondary metabolites are polar compounds and therefore are soluble in aqueous solvents. However, most alkaloids (e.g., serpentine, berberine and atropine), phenols (e.g., benzoquinones, coumarins and quinones), terpenoids (e.g., taxol, artemisinin) and polyacetylenes are nonpolar and therefore are most soluble in nonaqueous solutions.

In order to obtain enhanced amounts of a plant secondary metabolite, it is preferred that the tissue is differentiated (e.g., plant shoots and roots). Plant secondary metabolism is frequently linked to differentiation. Therefore, most undifferentiated cultures are not useful for producing secondary metabolites.

Many secondary metabolites are produced in plant roots. In addition, roots can be transformed into "hairy roots"; hairy roots are genetically stable, grow rapidly and produce levels of secondary products equal to or greater than the whole plant. Therefore, hairy root tissue is particularly useful for obtaining most plant secondary metabolites.

Hairy roots can be induced by genetic transformation (i.e., by introducing the Ri (root inducing) plasmid from Agrobacterium rhizogenes into plant seeds or root tissue) Hamill, D. et al., *Plant Cell Reports* 5:111–114 (1986). The production of hairy roots is partially a result of auxin regulation by this plasmid. A preferred method for transforming root tissue is explained in detail in Example 1. Transformation of root tissue by the Ri plasmid was found to be easier to accomplish and to result in greater rooting than transformation of germinated seedlings.

Most dicotyledonous plants producing secondary metabolites can be transformed. Some monocots and conifers are also transformable. Some plants are resistant to transformation by Agrobacteria species, but may be made susceptible to transformation through the use of virulence inducers, which are compounds, some produced naturally by susceptible plants, which have been found to promote transformation. Certain virulence inducers have proven especially useful in transforming gymnosperms, which are otherwise resistant, with A. tumefaciens, J. W. Morris and R. O. Morris *Proc. Natl. Acad. Sci. (USA)* 87:3614–3618 (1990).

In addition to producing enhanced levels of secondary metabolite and growing quickly, hairy root tissue may be better able to tolerate destabilization methods than normal differentiated tissue. For example, when tested, beet hairy roots were found to tolerate higher temperatures than normal beet roots. For beet roots, viability (measured as $CO_2$ evolution) began to decrease at 35°–40° C. However, for transformed hairy root tissue, $CO_2$ evolution did not begin to decrease significantly until treatment of 45° C. In addition, the rapid growth associated with transformation by Agrobacterium rhizogenes is believed to be due in part to endogenous control of auxin synthesis by the Ri plasmid. It is also known that plant regulators such as auxins can control polyamine biosynthesis, although the exact mechanism is not known. Polyamines are directly linked to stress tolerance in plants. Therefore, the transformation to hairy roots, besides improving growth, may also enable more vigorous destabilization methods to be utilized while still maintaining viability.

In order to obtain enhanced amounts of a plant secondary metabolite, the plant tissue should be actively synthesizing the metabolite or contain high levels of stored metabolite. Generally, plant cultures which are growing in late exponential growth phase and stationary phase produce enhanced amounts of a secondary metabolite. A particularly useful method of obtaining plant tissue, which contains enhanced amounts of secondary metabolite, is by culturing in a nutrient mist bioreactor (NMB), as described in U.S. Pat. No. 4,857,464 entitled "Mist Cultivation of Cells" by Weathers and Giles, the teachings of which are incorporated herein by reference. Cultivation of plant cells in a nutrient mist bioreactor offers the advantage of providing cells with a readily available gaseous and liquid nutrient supply. In addition, use of the bioreactor permits rapid change in culture conditions (e.g., nutrient or extractant addition) to allow for precise control of the culture environment. Further, in a bioreactor, cells are supported on screens within a sterile chamber which allows cell products and media to continuously drain away from the tissue into a collection chamber. In order to accommodate the growth of and extraction from transformed hairy roots, the Nutrient Mist Bioreactor should be modified as described in Example 2.

Although, cultivation in a nutrient mist bioreactor is a preferred method of obtaining tissue which produces high levels of secondary metabolites, for the purposes of the subject invention, any method of cultivation known in the art can be used. For example, cells can be grown on solidified agar gels or in liquid (suspension) cultures. Alternatively, the subject methods of extraction can potentially be performed on plants growing in the wild. In order to obtain enhanced amounts of a plant secondary metabolite, plant growth can be improved by adding plant growth regulators and hormones (e.g., cytokinins and auxins) and/or by optimizing environmental conditions such as temperature, light intensity, water stress, salinity, media composition and exposure to $CO_2$.

The following describes the results of experiments conducted to determine a method of obtaining enhanced amounts of secondary metabolites from beets with limited loss of beet tissue viability. The protocol for beet root disks is described in detail in Example 3 and for beet hairy roots in Example 4. The removal of secondary metabolites from beets represents a worst case scenario, and therefore is an ideal model system, since no basal release of secondary product occurs. Secondary metabolites in beets are stored intracellularly in vacuoles, requiring the traversal of 2 membranes before the metabolite can be released. Because the beet model represents the most difficult conditions for extracting secondary metabolites, the following results demonstrate the success of the present method for the extraction of secondary metabolite from virtually any plant cell tissue. In addition, the release of secondary metabolites (e.g., betacyanin, betanin, betaxanthins and betalamic acid) was easy to assay spectrophotometrically.

As used herein, the phrase "limited loss of tissue viability" refers to post-extraction viability in the range of about 80 to 100%, as measured by respiratory carbon dioxide evolution (from growing nonphotosynthetic tissue) and/or change in biomass (i.e., change in dry weight). Brodelius, P., *Appl. Microbiol. Biotechnol.* 27:561–566 (1988).

The viability of beet hairy roots is presented in terms of a viability index, V defined as:

$$V = \frac{(Z - X)}{(Y - X)} \times 100$$

where X, is the dry weight of the tissue prior to permeabilization (day 0); Y is the dry weight untreated tissue (day 3, approximately 1–1.5 doublings from day 0); and Z is the dry weight of treated tissue after permeabilization (day 3). The viability index has a variability of approximately 4%, which indicated that for $V \geq 96\%$, the tissue is considered to have been unaffected by the heat treatment. This value is determined by averaging the dry weights of the controls (% variability) in the heat treatment experiments. Viability measurements were taken over a relatively short period after destabilization (1–3 day). Brodelius found that for 3 days after the exposure to DMSO and Triton X-100, no growth occurred in suspension cultures of C. roseus, but that growth was reestablished relative to untreated controls after 4 days. Brodelius, P., *Appl. Microbiol. BioTechnol.* 27:561–566 (1988). Therefore, measuring viability at day 3, provides a worst case value.

Secondary Product Release From and Viability of Beet Root Disks

Beet root disks placed in the culture chamber of a nutrient mist bioreactor, released secondary product upon heating of the chamber and the incoming mist. The tissue treated at 35° C. released more product than the control (treated at 25° C.), which released some pigment even though the tissues were rinsed for 1 hr in cold running tap water. The tissues misted with B5 medium with 20 Mm additional $CaCl_2$ released less pigment than the control (treated at 25° C.). Secondary product release increased with increasing temperature, while viability, (measured as $CO_2$ evolution, post-heat treatment) decreased with increasing temperature. For both parameters, the effects were more pronounced at temperatures above 35° C.

Beet disks rinsed for 20 minutes with 20 mM $CaCl_2$ (in B5 medium) produced more $CO_2$ than disks not exposed to calcium regardless of treatment temperature, except at 55° C. At 25° C. the $CO_2$ production by disks treated with $CaCl_2$ was greater than that produced by disks with no $CaCl_2$ treatment. During the preparation procedure, the disks were cored from a tap root, then sliced into disks. This preparation may have stressed the tissue, and the difference noted at 25° C. was probably due to the improved membrane stability of the calcium treated disks.

The rate of decline of $CO_2$ production with increasing temperature was not as steep as for the tissues not rinsed with $CaCl_2$ post-heat treatment. At 55° C. however no $CO_2$ evolution was detected from any of the disks. The disks appeared bleached, having released all of their remaining pigment after 1 day on solid medium.

After 3 days, the tissues heated to 55° C. were visibly necrotic, while the tissues exposed to lower temperatures (40° C. to 25° C.) retained some membrane integrity evidenced by no further pigment leakage. Only the tissues rinsed with $CaCl_2$ suffered no additional pigment leakage 1 day after the 45° C. heat treatment.

Removal of the released product from beet root disks, during the heat treatment, was accomplished by exchanging the medium containing released product with fresh medium. The results indicate that as near continuous removal of released product is approached, pigment release relative to the controls (no rinses of tissue in the same medium volume), increased. For an extraction time of 8 minutes in a 20 ml volume, tissue rinsed 4 times (5 ml volume rinses) released 40% more product in the same time period. For longer extraction times of 60 minutes, the rinsed tissue (four 5 ml rinses) yielded the same amount of product released as the tissue that was not rinsed (20 ml volume). This equivalence of product release indicated that a concentration gradient began to effect the release of product as early as 15 minutes into the treatment period. Continuous rinsing occurs in the NMB, which can stimulate additional release.

Secondary Product Release From and Viability of Hairy Root Tissue

Hairy root tissue of safflower and beet were heat treated as described in Example 4. As was observed for beet root disks, secondary product release from beet hairy roots increased with increasing temperature, while viability decreased. However, hairy roots heated at 35° C. for 1 hr, unlike the disks, produced more $CO_2$ after 1 day than the same amount of root tissue cultured at 25° C. otherwise similarly treated. Based on the evolution of $CO_2$ from heated beet hairy roots, temperatures of 35°–45° C. were tested further for secondary product release while preserving viability.

Post-heat treatment of beet hairy roots with $CaCl_2$, for short exposures of 10, 20 and 60 minutes, improved viability. The improvements were determined by comparing the growth, post-heat treatment, of $CaCl_2$ treated tissue with tissue not exposed to $CaCl_2$ post-heat treatment. Although the cultures were at different stages of growth (5 days; mid exp. phase, 7 days; late exp. phase and 10 days; early stationary phase), the ratio of root mass to liquid volume was maintained constant. Failure to control this ratio produced inconsistent results since the tissues were not exposed to equal amounts of $CaCl_2$/gram of biomass. For longer exposures to $CaCl_2$ (>60 minutes), viability decreases. Finally, for exposures of 3 days (the entire recovery period), viability was less than the control. The control tissue was heat treated, but not exposed to $CaCl_2$ and by definition, is represented by a 0.0 gram dry weight change. The most effective exposures to $CaCl_2$, in terms of preserving viability, were: the 10 and 20 minute exposures for the 5 day (mid-exponential phase) culture, the 10 minutes exposure for the 8 day (late exponential phase) culture and the 20 minute exposure for the 10 day (early stationary phase) culture.

As percent of total betanin, the highest value of secondary product released from beet hairy roots (heated at 42° C. for 1 hr) was obtained from the 7 and 9 day cultures, at 15 and 14%, respectively. The viability indices for these heat treated cultures were 96 and 83%. Very little pigment (2% of total betanin; 2 $\mu$g) was released from the 5 day culture, which was in early exponential phase. The value of V for this culture was 84%.

Although the 11 day culture only released 12% of its pigment, the amount of pigment released was 3.6 times the amount released from the 7 day culture (44 $\mu$g vs 160 $\mu$g). The percentages of betanin released were based on 1.3 and 0.29 mg of total betanin contained in the 11 and 7 day cultures, respectively.

The ratio of tissue biomass to medium must be considered in order to isolate the differences, if any, between the stage of growth of the tissue and, in this case, pigment release. The betanin concentrations obtained after heat treatment of hairy roots in different volumes of media for the 7 day cultures indicate that a diffusion gradient began to restrict pigment release at betanin concentrations approaching 0.9 mg/l.

With increasing time of exposure to heat at 42°, 45° and 50° C., secondary product release from beet hairy roots increased. After heating at 42° C., secondary product release increased to 10% of total betanin after 20 minutes with no loss of viability. After heating at 45° C., V decreased to 80% after 2 minutes, while at 50° C., V was zero after 2 minutes of heating. The maximum temperature to which beet hairy roots could be heated while still retaining viability was 42° C.

The rates of betanin release from beet hairy roots increased with increasing treatment temperature. After just 10 minutes of heating, the concentrations of released product (in a 50 ml volume) were 0.25, 0.69 and 1.37 mg/l after heat treatments of 42°, 45° and 50° C., respectively. Similar results were also obtained for the other two beet pigments. After 45 minutes heating at 42° C., pigment efflux was no longer increasing at a linear rate. The concentration of betanin at this time was 0.9 mg/l. Based on the concentration of betanin released from 7 day cultures, further heating of the tissue at 42° C. would net a diminishing return in terms of product release vs. retention of viability.

Since viability of the heat treated tissue was not 100%, the source of the released pigment, whether from viable or non-viable (heat damaged) tissue, had to be determined. Using the method described in Example 4, the estimated pigment released from non-viable tissue vs. the actual pigment released, was calculated. In all cases, except for the 5 day culture, the actual pigment released was greater than the amount of pigment which was calculated to have been released from only the non-viable tissue. Furthermore, even under extreme conditions of heating (50° C. for 10 minutes; 100% non-viable tissue), beet hairy roots did not release all of their pigment, rather, only 25%. The assumption that the non-viable tissue released all of its pigment represents a worst-case scenario. Therefore, the actual pigment released from non-viable tissue must be less than the estimated value.

Production of secondary metabolite post-heat treatment was measured as described in Example 4. Heat treatments were performed on an 8 day culture at which time, 18% of the total product was released (0.097 mg betanin). After treatment with $CaCl_2$ and 3 days in culture, the tissue synthesized 0.71 mg of betanin compared to 0.74 mg from the tissue that was not heated. The net betanin produced by the heated tissue was 0.81 mg, a 9.5% increase in production over the non-heated tissue. This result demonstrates that removal of product can stimulate an increase in secondary metabolite production.

Secondary product release from beets was stimulated by treatment with $(NH_4)_2SO_4$ and EDTA. Treatments using B5 medium at pH values of 3.5 and 7.0, did not stimulate any product release. Ammonium sulfate concentrations up to 20 mM stimulated product release. The maximum product released was 12% of total betanin in 20 mM $(NH_4)_2SO_4$ after 2 hour extraction at 5° C. The viability index, determined 3 days after the heat treatment, decreased to 87%.

Five percent of total betanin was released after a 2 hour treatment with 1 mM $(NH_4)_2SO_4$ with no loss of viability. This effective concentration of $(NH_4)_2SO_4$ was achieved by excluding membrane stabilizers normally included in B5 medium (e.g., Ca and Mg). Concentrations of $(NH_4)_2SO_4$ greater than 20 mM decreased the amount of product released relative to the treatment using only 1 mM $(NH_4)_2SO_4$. Finally, the use of EDTA (1 mM), a calcium chelator, in addition to 20 mM $(NH_4)_2SO_4$, increased product release to 15% of total betanin with no additional loss in viability beyond 87%.

The rate of betanin pigment released from beets using ammonium sulfate treatments (20 mM) at 25° C. increased linearly up to 2 hrs. with an initial lag in pigment release of 15 minutes. The same result occurred with betaxanthin release. However, release of betalamic acid occurred immediately.

Betanin release was initiated in beet hairy roots cultured for 1 week in the nutrient mist bioreactor (See Example 4). From 1 gram dry weight of tissue, 18% of total betanin (0.49 mg) was released into the surrounding culture medium (865 ml) in two hours. Although the percent release of total product was higher than that obtained from shake flasks (15%), the ratio of tissue dry weight to medium volume must be considered. In shake flasks, the ratio was 2.0 g dry wt/l vs 1.16 g dry wt/l in the nutrient mist bioreactor (865 ml of B5+20 mM $(NH_4)_2SO_4$ was used in the extraction). In previous experiments in shake flasks using heat treatments at 42° C. to permeabilize the tissue, 15% and 23% of total pigment were released when the ratios of tissue to medium volume were 2.0 and 1.0 g/l, respectively. Therefore, product release in the culture chamber of the nutrient mist bioreactor can be directly compared to shake flasks containing equivalent tissue biomass to extraction medium volume ratios.

Viability of the tissue after the heat treatment was again comparable to the value obtained from shake flasks. The viability index was 84% for the tissue treated in the nutrient mist bioreactor vs. 87% for the tissue treated in shake flasks.

Applicability of Extraction Methods to Other Plant Tissue

The results of experiments using beet root disks and beet hairy roots are applicable for extraction of plant secondary metabolites from any other plant tissue. The properties of plant cell membranes and in fact all eukaryotic cell membranes are universal. All biological membranes, including the plasma membrane and the internal membranes of eukaryotic cells, have a common overall structure; they are assemblies of lipid and protein molecules held together by noncovalent interactions. The lipids are arranged as a bilayer, which provides the basic structure of the membrane and serves as a relatively impermeable barrier to the flow of most water-soluble molecules. The protein molecules are within the lipid bilayer and mediate the various functions of the membrane; some service to transport specific molecules into or out of the cell; (e.g., channel proteins, such as passive channel proteins, carrier proteins, and proteins involved in active transport) others are enzymes that catalize membrane-associate reactions; and still others serve as structural links between the cell's cytoskeleton and the extracellular matrix, and or as receptors for receiving and transducing chemical signals from the cell's environment.

Therefore, methods of destabilizing and restabilizing beet cell membranes will produce the same effects when used on other plant cell tissue. The beet model results show that plant tissue membranes can be destabilized using any of a number of techniques performed alone or in combination. For example, the tissue can be exposed to elevated temperatures for various periods of time. Culturing plant tissue in temperatures ranging from 25°–45° for times ranging from about 1 minute-to two hours increases the fluidity of plant cell membrane and is therefore useful for obtaining partial release of most secondary metabolites, while maintaining plant tissue viability. Viability generally decreases with length of exposure to the method of permeabilization. The optimal temperature and time of exposure can be determined by one of skill in the art without requiring undue experimentation.

Alternatively, destabilization can be accomplished by contacting plant membranes with a permeabilizing agent (i.e., a substance which fluidizes a channel protein within a plant cell membrane) at an appropriate temperature and for an appropriate amount of time. Shorter exposures to the permeabilizing agent, (e.g., 1 min to 2 hrs) result in minimal loss of viability.

Examples of permeabilizing agents are substances which prevent the binding of divalent cations to plant cell membranes. Divalent cations stabilize cell membranes by reducing the electrostatic repulsion between ionic centers on the membrane. Siegel, S. M. and O. Daly *Plant Phys.* 41:1429–1434 (1966). Therefore, any substance, which prevents the binding of divalent cations destabilizes and permeabilizes the membrane. The order of effectiveness for destabilizing beet plant cell membranes by preventing divalent cation binding to the plant cell membrane is that removal of manganese destabilizes better than removal of calcium, which is better than removal of strontium, which is better than removal of barium, which is better than removal of magnesium (i.e., $Mn > Ca > Sr > Ba > Mg$). This order of effectiveness should prove to hold true for all plant cell membranes.

Additional examples of permeabilizing agents include compounds which contain the ammonium ion-(e.g, $(NH_4)_2SO_4$, especially in concentrations ranging from 1 to 20 mM) and (ethylenediamine) tetraacetic acid trisodium salt (EDTA) which is a chelator of divalent cations (4 EDTA molecules chelate 1 divalent cation). Since divalent cations stabilize membranes, chelating any free divalent cations away from the tissue, indirectly permeabilizes the membrane, increasing product release.

Membrane destabilization can also be accomplished by excluding membrane stabilizers, such as methods of divalent cations, from the culture medium. For example, culturing plant tissue in medium that lacks membrane stabilizers such as $Mg^{+2}$ or $Ca^{+2}$, or both, can result in release of secondary metabolites from the plant tissue. For plant tissue which is not growing in an NMB, controlled electroporation and/or sonication can be used to destabilize plant cell membranes.

The results of beet root experiments indicate that different secondary metabolites are released at different rates as a result of different destabilization methods. For example, the rate of betanin and betaxanthin pigments released from beets using ammonium sulfate treatments (20 mM) at 25° increased linearly up to 2 hrs. with an initial lag in pigment release of 15 minutes. However, release of betalamic acid occurred immediately. The degree of selectivity toward specific products offered by the choice of destabilization methods provides additional control over process development. The choice of which destabilization method to employ to extract a particular secondary metabolite, as well as optimization of the conditions used, such as time of exposure and temperature, can be determined by one of skill in the art without undue experimentation.

Subsequent to destabilizing the plant membrane, a solvent can be added to the culture medium in order to effect greater extraction. For example, some secondary metabolites (e.g., taxol and artemisinin) are nonpolar compounds and therefore are non-soluble in aqueous solutions, such as the culture medium. Therefore, a nonaqueous solvent can be added to the culture medium to enhance extraction of nonpolar secondary metabolites. Preferred nonaqueous solvents include: ethanol, 65% and 75%, polyethylene glycol (PEG-400), tomatine, poly-L-Lysine, 50% Cremaphor EL in a short chain alcohol (e.g., methanol), DMSO, Triton X-100, Brij Tween-80 and cumene peroxide. Ethanol and 50% Cremaphor EL in methanol or in any other short chain alcohol are particularly useful for extracting taxol from Taxus species. Alternatively, the permeabilizing agent itself can be a nonaqueous solvent.

However, it is important that the particular solvent used does not decrease the plant tissue viability. Example 5 presents experiments, which tested the effect of nonpolar solvents in combination with heat treatment on plant cell viability. The results of the experiment indicate that tissue which is treated with lower temperatures (e.g., 25° C.) and shorter times of exposure (e.g., 1–35 mins) released more secondary metabolite, while maintaining tissue viability.

In the final step of the method of the invention, plant tissue membrane is restabilized to stop secondary metabolite release and to enhance plant tissue viability. The results of the beet root experiment show that plant tissue membranes can be restabilized using any of a number of techniques performed alone or in combination. One approach is to remove the condition which promoted destabilization. For example, if destabilization was caused by raising the temperature of the culture medium, restabilization can be effected by cooling the culture medium (e.g., to room temperature), to return the fluidity of the plant cell membrane to its normal level. Alternatively, the destabilizing agent can be removed. Further, divalent cations can be introduced into cultures which were destabilized by being cultured in medium which lacked divalent cations or in medium which contained a permeabilizing agent. The order of effectiveness for restabilizing plant cell membranes by introducing divalent cations into the medium, so as to make them available for binding to the plant cell membrane, is the same for the order of effectiveness for destabilizing by removal (i.e., $Mn > Ca > Sr > Ba > Mg$). Addition of substances which intercalate into the lipid bilayer, such as sterols (e.g., cholesterol, B-sitosterol, and stigmasterol), phospholipids, or glycolipids and/or glycoproteins can also effectively restabilize plant cell membranes.

The present invention will now be illustrated by the following Examples, which are not to be seen as limiting in any way.

EXAMPLE 1

Method of Obtaining Hairy Roots

Maintenance of Agrobacterium rhizogenes strains

Agrobacterium rhizogenes strain ATCC 15834 was maintained on YMB medium (in g/l: $K_2HPO_4$-0.5, $MgSO_4.7H_2O$-2.0, NaCl-0.1, Mannitol-10.0, yeast extract-0.4, and agar-15.0, pH 7.0) at 25°–28° C. Only fresh (2–3 days old) cultures subcultured directly from the original stock were used for purposes of infecting tissue since the bacteria lose their virulence after successive subculturings.

Hairy root initiation using beet root disks

Garden variety beets (Detroit dark red) were harvested, the stems and leaves were cut away and the beets were scrubbed under running tap water to remove surface dirt. The whole beets were surface sterilized in 10% commercial bleach (Clorox) for 30 minutes. The area to be cored was cut away and discarded, and the beet was placed in 10% bleach for 20 minutes more. The area to be cored was again cut away and discarded. A sterile cork borer (1.5 cm diameter) was forced through the center of the beet. It was necessary to manually hold the beet (without gloves) at this point since forceps and gloves proved ineffective. The ends of the corings were cut off and discarded and the remaining core was placed in sterile distilled water. The cores were sliced into disks approximately 3 mm thick, rinsed three times with sterile distilled water in sterile Petri dishes and blotted dry on sterile Whatman #1 filter paper. The disks were placed on solid B5 salts with 0.2% Gel-rite, 20 g/l sucrose and 0.025% (w/v) carbenicillin (Pfizer). The disks were infected with A. rhizogenes by swabbing the surface of the disk with a sterile toothpick which had been dipped in a 2–3 day old bacterial culture grown in Petri dishes. Typically, 3 disks were placed on each plate; 2 of these were infected and the third was left as a control. After approximately 2 weeks, roots began to grow from the site of the infection.

Obtaining axenic hairy root cultures of Beta vulgaris

After excising the roots from the primary explant, the tissue was cultured on solid B5 media with 20 g/l sucrose+0.025% carbenicillin. According to Flores, et al., roots growing up off the agar surface will be free of contamination (Flores H. E., et al., Trends in Biotechnology 64–69 (1987)) and can be subcultured to obtain an axenic culture. This method was ineffective for beet hairy roots probably due to the excessive root hairs which could have trapped and carried contamination off the surface of the Gel-rite. The tissue, although contaminated, was cultured in liquid B5 media (B5 salts+B5 vitamins+30 g/l sucrose, pH 5.5–6.0) containing 0.025% carbenicillin for up to 2 weeks. (Liquid B5 media, unless otherwise specified contains 30 g/l sucrose, B5 salts and vitamins at a pH of 5.5–6.0). This procedure increased the amount of tissue enabling a variety of harsh tissue sterilization treatments to be performed without danger of losing the transformed tissue. Hairy roots were then blotted dry on sterile Whatman #1 filter paper and subcultured onto solid media with 0.25% carbenicillin. After about 1–2 weeks, these tissues were subjected to dips in commercial bleach (3–10% Clorox) for periods of up to 10 minutes. The tissues were then rinsed in sterile deionized water, blotted dry as previously described and placed on solid media with 0.25% carbenicillin. This procedure was repeated until no contamination was visible in subsequent liquid cultures without antibiotics for 2 weeks.

EXAMPLE 2

Modifications to the Nutrient Mist Bioreactor to Accommodate the Growth of Transformed Hairy Roots Modification 1

Increasing the Mist Volumetric Throughput

The mist volumetric throughput can be increased by placing the ultrasonic transducer inside the culture chamber (i.e., either at the top [which is preferred] or the bottom). The theoretical transducer output is 575±175ml/hr. The growth results were obtained with a mist flow of 12 ml/hr. The mixing time for the culture changes containing roots calculated for these conditions was 63 minutes, which means that 3 hours are required for 95% turnover of the retained liquid by the roots in the culture chamber. In order to remove released product as well as to treat with a restabilizing agent, too much time would be needed and the tissue would probably die in the process. For this reason, tissue cultured in the growth chamber was destabilized as follows:

Beet hairy root tissue was cultured for 1 week in the NMB. NMB was operated in 2 different configurations: continuous mode (no medium recycle) and batch mode (recycle of nutrient mist and coalesced medium from the culture chamber into the medium reservoir). Different culture conditions were established based on varying the following parameters: mist cycle time (range of 5/6 to 5/20, and 2/2 to 2/10), mode of operation (batch or continuous), inoculum size and sucrose concentration in B5 medium for beets (10-35 g/l). (A mist cycle denoted as 5/6 represent a repeating cycle of 5 minutes of misting followed by 6 minutes without misting). Carbon dioxide enhancement (1.0%) of the carrier gas (air) was also performed. The best conditions for growth were determined by comparing dry weight increases after 1 week in culture. Secondary metabolite production was also measured, using a small representative sample (approx. 1-2 grams wet weight) of the total root mass.

Beet hairy root tissue growth was monitored as fresh weight increases. The entire culture chamber (sterile and loaded with tissue) was placed on a Mettler top loading balance (2600 kg maximum load). Growth was measured beginning at 3 days after inoculation as an equilibration time was necessary for coalesced medium to achieve a steady state within the culture chamber. The balance was tared to zero each day, and the subsequent weight increases were recorded. Dry to wet weight correlations for the tissue in the culture chamber were obtained by comparing the 1 week values of dry tissue.

After 1 week, the culture chamber effluent was clamped off and a vent was opened at the top of the culture chamber. Fresh B5 liquid medium without $CaCl_2+20$ mM $(NH_4)_2SO_4$ was pumped into the culture chamber through sterile tubing, until the liquid level was just above the tissue in the nylon matrix. After 2 hours of exposure, the culture chamber was drained, then filled as before with B5 liquid medium $+20$ mM $CaCl_2$ and immediately drained. The normal misting cycle was resumed, and the tissue was cultured with 30 g/l sucrose in B5 medium. After the second week of growth, the tissue was analyzed for pigment production and growth. The residence time could be reduced to 1-2 minutes with the proposed modification. Therefore, product release and recovery could be accomplished using nutrient mist.

The increased availability of mist will also allow smaller air volumes (carrier gas) to be used since the mist does not have to be transported from the mist generator to the culture chamber. Reduced air volumes reduces the effect of medium acidification that was noted after operating the bioreactor in a recycle configuration. Mist distribution in the modified design could be carried out by rotating the support trellis. Another method of mist distribution could be to have the exit from the culture chamber just above the top of the support trellis. This would force the entire culture volume to be covered with mist, and coalesced mist would be effectively recycled since the medium reservoir is, in effect, at the bottom of the culture chamber. If desired, media recycle, or fresh media can be added by simultaneously draining and adding sterile nutrient media from the sump at the bottom of the culture chamber. Air enriched with $CO_2$ could be added during the off cycle to minimize medium acidification due to dissolved $CO_2$ in the medium.

Increased mist volume may enable the culturing of root tips which would greatly improve the rate of biomass production in the nutrient mist bioreactor. In the past root tips could not be used as inocula for the bioreactor because of a naturally produced mucilage layer which prevented nutrient uptake. The increased mist flow (liquid contact) could wash away this layer (as it is washed away in liquid culture) and allow for the culture of rapidly growing root tips.

Finally, in order to scale-up the culture chamber volume, increased flow, which is only possible by the proposed modification, is vital. In the previous design, substantial coalescence of the generated mist occurs in the mist generator (specifically, at the orifice). For liquid throughput determinations, the wider the internal diameter, the better the throughput.

Modification 2

A collapsible trellis in the culture chamber for use in scale-up.

Inoculation of the 2 liter culture chamber with hairy root tissue can be accomplished by simply removing the lid (in a sterile hood) and placing the tissue directly on the 3 levels of nylon mesh. To scale up, this method is both inefficient and ineffective, because it requires considerable skilled manual labor and the size limits the ability to load roots aseptically. In addition, the time required for large numbers of roots means early loaded roots will have desiccated. By using a collapsing trellis suspension of hairy roots could be pumped into the bottom of the culture chamber to effectively load each level. The top level can be raised (containing the tissue), and the procedure can be repeated for the next level until the entire trellis has been raised. Lowering and raising of the trellis can be accomplished without breaching the internal sterile environment. A magnetic coupling on the side of the culture chamber could be used to raise and lower the trellis or the trellis position could be controlled pneumatically.

EXAMPLE 3

Secondary Product Release From and Viability of Beet Root Disks

Growth of beet root disks in the nutrient mist bioreactor.

A cork borer (1 cm diameter) was used to obtain uniform disks from washed and peeled garden variety beets (Detroit Dark Red). The disks were sliced approximately 3-5 mm thick, rinsed in running tap water for 1 hour and blotted dry. The Nutrient Mist Bioreactor (NMB, Mistifier TM) (Bio-Rational Technologies, Stow, Mass.) was configured in a continuous flow mode and 12 pre-weighed disks were placed in the nylon matrix which was then placed into the polycarbonate chamber (pre-heated to 35° C. in a Lab-Line incubator). The culture chamber containing the disks was returned to the incubator.

The chamber was misted on a 5/10 cycle using preheated B5 medium (35° C.), with an air flow of 1400 ml/min. After 1 hour, the disks were removed and placed in 2 ml of B5 medium. After 30 seconds, the disks were removed and the liquid was assayed for released pigments based on individual absorbance maxima for each of the three major beet pigments. The disks were then ground, the pigments were extracted and assayed by measuring an absorption spectrum (380-640 nm) of a 1 ml sample containing released pigment in a Beckman DU-64 recording spectrophotometer (slit dimensions 0.3 mm wide×2 mm high). Absorbance values from 380–640 nm were measured over 10 nm increments as well as at the absorbance maxima for the pigments (426, 478, and 537 nm, for betalamic acid, betaxanthins and betanin, respectively). (Saguy I. Mizrahi S. and I. J. Kopelman, *Journal of Food Science* 43:121–123 (1978)). Culture media was used as a blank. The error or drift in the reading over the entire spectrum using the blank was no more than 0.002 absorbance units.

Betacyanin was assayed using the methods of Saguy, et al., to resolve the individual pigment concentrations within the mixture. (Saguy I., Kopelman I. J., and Mizrahi S., *Journal of Food Science*, 43:124–127 (1974)) The procedure was repeated using 12 different disks at a temperature of 25° C., as a control measure. The experiment was also performed using B5 medium with an additional 20 mM $CaCl_2$ preheated to 35° C. (12 different disks) in the mist generator.

Secondary product release and viability of beet root disks after heat treatment in B5 medium Sterile beet root disks were obtained as described in Example 1. The disks were weighed and 6 disks were placed into a series of sterile, 1×10 cm test tubes. The total wet weight of the disks in each of the tubes (2 g) was kept within 5%. Sterile B5 medium (3 ml) was added to each test tube. The test tubes were placed in heating blocks at temperatures ranging from 25° C. (ambient) up to 55° C. for periods of 15, 30 and 45 minutes. After the specified time had elapsed, the sterile tissues were removed and rinsed 3 times with sterile distilled water in Petri dishes. The tissues were blotted dry and placed into T25 tissue culture flasks containing 20 ml of solid B5 medium. The flasks were sealed with a rubber septum and incubated in the dark at 25° C. After 5 days, 200 μl of gas was removed from each flask and assayed for $CO_2$ using gas chromatography. Patriquin, D. and Knowles, P. *Canadian Journal of Microbiology* 20:1037–1041 (1974). This experiment was repeated using B5 medium +20 mM $CaCl_2$ in the heating medium.

Application of $CaCl_2$ to enhance viability after heat treatments

Beet root disks were heated to release secondary product as described above with the following modifications: 1) After coring the beets, all subsequent rinses of the tissues were performed using half strength B5 medium so as not to stress the tissue causing product release. 2) After the heat treatments, the tissues to be treated with $CaCl_2$ were placed on solid B5 medium (in T25 flasks) containing an additional 20 mM $CaCl_2$. 3) Five, rather than six disks were used in each flask. 4) Carbon dioxide concentrations were measured daily over a 4 day period after the heat treatment.

The experiment described here was repeated a third time with the additional modification of rinsing the tissue after the heat treatment. The tissues to be treated with $CaCl_2$ were rinsed in B5 medium+20 $CaCl_2$. The other tissues were rinsed in standard B5 medium.

Secondary product release from beet root disks with rinsing cycles.

Beet root disks (1 cm×2–3 mm) were rinsed in running tap water for 1 hr, blotted dry, weighed and placed in sterile 1×10 cm test tubes (3 disks/tube). The total disk weight/tube was kept to within 10%. Preheated MS media (Murashige T and F. Skoog *Physiologia Plantatum* 15:473–482 (1962)) (40° C.) was added to each tube and the tubes were placed in heating blocks at 40° C. for periods of 8, 16 and 60 minutes with periodic rinsing cycles according to Table 2. The total volume of releasing buffer (MS media pH 6.0) was kept constant at 20 ml. The controls for this experiment involved exposing equivalent amounts of tissue to the entire treatment volume (20 ml) for 8, 16 or 60 minutes (labeled "b" in Table 1). After the tissues were rinsed, the control disks were dried and the average dry weight was calculated.

TABLE 1

Procedural summation for the periodic rinsing of beet root disks.

| Sample No. | Time Between Rinses (min) | No. of Rinses | Vol. Used/ Rinse (ml) | Total Time | Total vol. (ml) |
|---|---|---|---|---|---|
| 1a | 2 | 4 | 5 | 8 | 20 |
| 1b* | — | 0 | 20 | 8 | 20 |
| 2a | 4 | 4 | 5 | 16 | 20 |
| 2b* | — | 0 | 20 | 16 | 20 |
| 3a | 15 | 4 | 5 | 60 | 20 |
| 3b* | — | 0 | 20 | 60 | 20 |

*The tissues were not passed through multiple rinses, but were exposed to the same total volume as the rinsed tissue.

The disks (5 for each experimental condition) were treated with preheated (35° C.) B5 medium containing 30 g/l sucrose.

EXAMPLE 4

Secondary Product Release From and Viability of Beet Hairy Root Tissue

Heat treatment of beet hairy root tissue and the effect of exposure to $CaCl_2$ on viability Beet hairy root tissue (0.3 g wet wt.) was cultured in 50 ml B5 liquid media for 5, 7, 8, 9, 10, or 11 days. After the initial growth period, spent medium was removed aseptically and 50 ml of preheated B5 liquid medium (42° C.) was added to each flask (Table 3). For the cultures grown 5, 8 and 10 days, the preheated medium added to each flask was adjusted to maintain a constant ratio of tissue wet weight to treatment medium volume (based on 50 ml added to the 8 day culture). The cultures were incubated for 1 hr at 42° C., then the released product was assayed spectrophotometrically as explained in Example 3. Tissues were treated with 20 mM $CaCl_2$ for 10', 20', 60' or 3 days. For the tissues not treated 3 days, fresh B5 liquid medium was exchanged aseptically and the roots were cultured 3 days at 25° C. at which time dry weights were measured. Experimental controls were provided. A set of 2 control flasks were routinely used for each condition in this and all experiments.

Heat treatment of beet hairy roots at a range of temperatures and exposures.

Beet hairy root tissue (0.3 g wet wt.) was cultured in 50 ml B5 liquid medium for 7 days. Spent media was removed and replaced with 50 ml of preheated, B5 liquid media at temperatures of 25°, 35°, 40°, 42°, 50°, or 55° C. for 30, 45 or 60 minutes. Heat treatments at 42° C. were also performed on 1 week old cultures using 25 and 100 ml of preheated B5 medium. Treatment medium was removed, assayed for betacyanins and replaced with fresh B5 liquid media+20 mM CaCl$_2$ for 10 minutes. Then the CaCl$_2$ medium was replaced with fresh B5 liquid medium and the tissues were cultured an additional 3 by days before measuring dry weights. Experimental controls (similarly cultured prior to the onset of heat treatment), included: 1) root tissue which was not heat treated but was otherwise treated exactly the same as the heated tissue, and 2), root tissue which was not heat treated, but instead of removing the spent medium, the tissue was cultured with no medium exchanges.

The source of the released pigment, whether from viable or non-viable tissue, was estimated by making the following assumptions; 1) The pigments were uniformly distributed throughout the tissue biomass. 2) The percentage difference between the dry weight of the heated tissue vs. the non-heated tissue represented non-viable tissue. 3) The non-viable tissue released all of its pigment. This amount of pigment was calculated based on assumption 1). Finally, the pigment released by the non-viable tissue (Pnv) was compared to the actual pigment released (P) at 42° C., after 1 hour. If P>Pnv, then some of the released pigment had to have been released from viable tissue.

Secondary metabolite production and growth after heat treatment

A series of flasks containing 50 ml B5 liquid medium were inoculated, cultured and heat treated at 40° C. as described above, but after the heat and CaCl$_2$ treatments, the spent medium removed prior to heating was returned to the flasks aseptically. Another series of flasks were also heated, but after the CaCl$_2$ treatment, fresh B5 liquid medium was added.

At the time of the heat treatment and every day afterward up to 3 days, 2 flasks of each type (fresh medium and spent medium) were sacrificed. The tissue from flask #1 was blotted dry, weighed (fresh weight), then ground for total pigment extraction and analysis as described above. The tissue from flask #2 was blotted dry, weighed (fresh weight), dried at 60° C. overnight and weighed again (dry weight). The fresh weight and dry weight of #2 were used, along with the fresh weight of #1, to determine the dry weight of #1.

Treatment of hairy root tissues with (NH$_4$)$_2$SO$_4$, EDTA and varying medium pH values.

The procedure for heat treatment described above was followed with the exception that instead of heating, the tissue was treated in one of the following variations of B5 media for 2 hrs: 1) B5 liquid medium without CaCl$_2$ or Mg, 2) B5 liquid medium without CaCl$_2$ +magnesium 5, 10, 15, 20, 25, 40, 60, 80 or 100 mM (NH$_4$)$_2$SO$_4$, 3) B5 liquid medium, pH 4.0, 6.5 or 7.5, and 4), B5 liquid medium+20 mM (NH$_4$)$_2$SO$_4$+1, 3 or 4 mM EDTA. Also, as described above, the release of product over time (30', 60', 90' and 120') was measured. After treatment for product release, the tissues were treated with CaCl$_2$, etc. as described above.

EXAMPLE 5

Effect of Non-Polar Solvents on Plant Cell Viability

To test the effect that non-polar conditions have on plant cell viability, beet root disks were incubated in a solution containing 50% Cremaphor EL and 50% methanol and incubated for various periods of time at the following temperatures: 25° C., 35° C., and 40° C. Since beet disks are mature tissue, which therefore do not increase biomass, viability was measured in terms of carbon dioxide respiration. Because different beet root disks were used for the various times and different temperatures, the left side of the table indicates the dry weight of the beet disk used and the right side indicates the respiration measured for that amount of beet root disk.

Disks which were incubated in 50% Cremaphor EL and 50% methanol at 25° C. had the greatest viability relative to those incubated at 35° C. and 45° C. The data which were obtained are presented in Table 2. Qualitatively, red pigment appeared to leach out of the disks much more quickly in disks which were treated with lower temperatures and shorter times of exposures. This phenomenon manifested itself as a lack of red pigment in incubation media of the T25 flasks as well as in the disks which implies that the pigment left the disks upon rinsing. In the medium of these disks, there was still a predominance of yellow pigment. The plates which were exposed for longer periods of time and/or at higher temperatures had medium which was predominantly red in color, although it was not possible to determine the presence of yellow pigment because it was overshadowed by the red pigment.

TABLE 2

Heat Treatment of Beet Root Disks Incubated in a Solution Containing 50% Cremaphor EL and 50% Ethanol

| | Dry Weight (g) | | | % CO$_2$ Released | | |
|---|---|---|---|---|---|---|
| Minutes | 25° | 35° | 45° | 25° | 35° | 45° |
| 0 | .0702$^y$ | n.d. | n.d. | 12.79 | n.d. | n.d. |
| 5 | .0766$^y$ | .0583$^y$ | .0593$^y$ | 11.11 | 7.25 | 11.18 |
| 15 | .0646$^y$ | .0629$^y$ | .0569$^r$ | 10.80 | 6.45 | .75 |
| 30 | .0597$^y$ | .0588$^r$ | .0565$^r$ | 10.58 | 4.43 | .51 |
| 45 | .0604$^r$ | .0546$^r$ | .0505$^r$ | .537 | .19 | .63 |
| 60 | a | .0576$^r$ | .0475$^r$ | a | .23 | .44 | n.d. = not determined
a = this sample was contaminated
y = yellow pigment was predominant in incubation media
r = red pigment was predominant in incubation media Equivalents Those skilled in the art will recognize, or be able to ascertain using no more than routine experimentation, many equivalents to the specific embodiments of the invention described herein. Such equivalents are intended to be encompassed by the following claims.

We claim:

1. A process for extracting enhanced amounts of a plant secondary metabolite from plant tissue with limited loss of plant tissue viability, comprising the steps of:
   a. permeabilizing a differentiated cultured plant tissue membrane to effect partial release of a plant secondary metabolite from the plant tissue;
   b. separating the secondary metabolite from the plant tissue surroundings; and
   c. depermeabilizing the plant tissue membrane to substantially inhibit secondary metabolite release, thereby preserving plant viability and permitting additional secondary metabolite synthesis,
   whereby the plant secondary metabolite is separated from the plant tissue with limited loss of plant tissue viability.

2. A process of claim 1, wherein step a is accomplished by exposing the plant tissue membrane to a temperature between approximately 25° C. and approximately 55° C. for a period of time sufficient to effect partial secondary metabolite release from the plant tissue with limited loss of plant tissue viability; and step c is accomplished by cooling the plant tissue membrane to ambient culture temperature for a period of time sufficient to effect depermeabilization and limited loss of plant tissue viability.

3. A process according to claim 2, wherein the plant tissue membrane is exposed to a temperature between approximately 25° C. and approximately 55° C. for a period of time between approximately 1 minute and approximately 2 hours.

4. A process of claim 1, wherein step a is accomplished by contacting the plant tissue membrane with a permeabilizing agent; and step c is accomplished by removing the permeabilizing agent introduced in step a.

5. A process of claim 4, wherein the permeabilizing agent is a substance which prevents the binding of divalent cations to plant cell membranes.

6. A process of claim 1, wherein step a is accomplished by excluding a membrane stabilizer from the culture medium, and step c is accomplished by adding the membrane stabilizer which was excluded in step a.

7. A process for extracting enhanced amounts of a nonpolar plant secondary metabolite from plant tissue with limited loss of plant tissue viability, comprising the steps of:
   a. permeabilizing a differentiated cultured plant tissue membrane to effect partial release of a nonpolar plant secondary metabolite from the plant tissue;
   b. contacting the plant tissue membrane with a nonaqueous solvent which does not decrease plant tissue viability, thereby producing solvent containing the nonpolar secondary metabolite;
   c. separating the solvent containing the nonpolar secondary metabolite from the plant tissue surroundings, thereby separating the released nonpolar secondary metabolite from the plant tissue surroundings; and
   d. depermeabilizing the plant tissue membrane to substantially inhibit secondary metabolite release,
whereby the plant secondary metabolite is separated from the plant tissue with limited loss of plant tissue viability.

8. A process of claim 7, wherein in step b, the nonaqueous solvent is selected from the group consisting of: ethanol, 65% and/or 75% polyethylene glycol (PEG-400), tomatine, poly-L-Lysine, 50% Cremaphor EL in a short chain alcohol, DMSO, Triton X-100, Brij, Tween-80 and cumene peroxide.

9. A process for extracting enhanced amounts of a nonpolar plant secondary metabolite from differentiated cultured plant tissue with limited loss of plant tissue viability, comprising the steps of:
   a. permeabilizing a plant tissue membrane by contacting the membrane with a permeabilizing agent selected from the group consisting of: ethanol, 65% and/or 75% polyethylene glycol (PEG-400) tomatine, poly-L-Lysine, 50% Cremaphor EL in a short chain alcohol, DMSO, Triton X-100, Brij, Tween-80 and cumene peroxide for a length of time sufficient to effect partial release of a plant secondary metabolite from the plant tissue With a limited loss of plant tissue viability, thereby producing a permeabilizing agent containing the nonpolar secondary metabolite;
   b. separating the permeabilizing agent containing the nonpolar secondary metabolite from the plant tissue surroundings, thereby separating the released nonpolar secondary metabolite from the plant tissue surroundings; and
   c. depermeabilizing the plant tissue membrane to substantially inhibit secondary metabolite release,
whereby a nonpolar plant secondary metabolite is separated from the plant tissue with limited loss of plant tissue viability.

10. A process for extracting enhanced amounts of taxol or a taxol-like compound from a Taxus species with limited loss of Taxus species viability, comprising the steps of:
   a. permeabilizing a differentiated cultured Taxus tissue membrane to effect partial release of the taxol or taxol-like compound from the Taxus tissue;
   b. contacting the Taxus tissue membrane with a nonaqueous solvent which does not decrease plant tissue viability to the plant tissue surroundings, thereby producing a nonaqueous solvent containing taxol or a taxol-like compound;
   c. separating the nonaqueous solvent containing the taxol or taxol-like compound from the plant tissue surroundings; and
   d. depermeabilizing the Taxus tissue membrane to substantially inhibit release of taxol or taxol-like compounds,
whereby the taxol is separated from the plant tissue with limited loss of plant tissue viability.

11. A process of claim 10 wherein the nonaqueous solvent is Cremaphor El in a short chain alcohol.

12. A process of claim 10, wherein in step b, the nonaqueous solvent is selected from the group consisting of: ethanol, 65% and/or 75% polyethylene glycol (PEG-400), tomatine, poly-L-Lysine, 50% Cremaphor EL in a short chain alcohol, DMSO, Triton X-100, Brij, Tween-80 and cumene peroxide.

* * * * *